(12) United States Patent
Ikegame

(10) Patent No.: US 9,041,351 B2
(45) Date of Patent: May 26, 2015

(54) ELECTRONIC CASSETTE CHARGER

(75) Inventor: Haruka Ikegame, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 711 days.

(21) Appl. No.: 13/341,288

(22) Filed: Dec. 30, 2011

(65) Prior Publication Data

US 2012/0194132 A1 Aug. 2, 2012

(30) Foreign Application Priority Data

Jan. 27, 2011 (JP) ................. 2011-015502

(51) Int. Cl.
*H02J 7/00* (2006.01)
*A61B 6/00* (2006.01)

(52) U.S. Cl.
CPC ............. *H02J 7/0045* (2013.01); *A61B 6/548* (2013.01)

(58) Field of Classification Search
CPC ...... H02J 7/0042; H02J 7/0044; H02J 7/0045
USPC .......................... 320/107, 113, 115
See application file for complete search history.

(56) References Cited

U.S. PATENT DOCUMENTS 5,525,888 A * 6/1996 Toya ........................ 320/111
6,127,802 A * 10/2000 Lloyd et al. ............... 320/113

FOREIGN PATENT DOCUMENTS

| JP | 463564 U | 5/1992 |
| JP | 2004101559 A | 4/2004 |
| JP | 2010154912 A | 7/2010 |
| JP | 2010214108 A | 9/2010 |
| JP | 2010-276687 A | 12/2010 |

OTHER PUBLICATIONS

Notification of Reasons for Refusal, dated Jan. 23, 2013, issued in corresponding JP Application No. 2011-015502, 4 pages in English and Japanese.

* cited by examiner

*Primary Examiner* — Edward Tso
*Assistant Examiner* — Aaron Piggush
(74) *Attorney, Agent, or Firm* — Sughrue Mion, PLLC

(57) ABSTRACT

A charger includes a loading chamber into which a battery pack is insertably/removably loaded. An insertion opening into which the battery pack is inserted is formed on an upper surface of the main body. The loading chamber is forwardly inclined to a front surface of the main body, and a bottom surface of the insertion opening is inclined with respect to a horizontal direction so that one end of the front surface side is located at a lower end and the other end of the back surface side is located at an upper end. A connector for supplying power is disposed at the upper end side of the bottom surface. Even when the dust, rubbish or fluid entered from the insertion opening drops to the bottom surface, it flows down to the lower end side, so that less dirt adheres to the connector.

12 Claims, 7 Drawing Sheets

ELECTRONIC CASSETTE CHARGER

FIELD OF THE INVENTION

The present invention relates to an electronic cassette charger for charging an electronic cassette used in radiography.

BACKGROUND OF THE INVENTION

In radiography, for example, X-ray imaging, a transportable electronic cassette is used instead of an X-ray film. The electronic cassette detects an X-ray image showing image information of an object through X-rays transmitted through the object. The electronic cassette contains a flat panel detector (FPD: Flat Panel Detector) capable of outputting X-ray imaging data as digital data.

The electronic cassette is attached to a stationary platform for photographing a patient in standing posture or supine posture. The electronic cassette is also used in other situations, for example, photograph of joint of elbow or knee of patient, photograph of a patient on a bed in a hospital room, who has difficulty to move to a photo studio, or photograph of the patient on a wheelchair in an emergency situation.

JP-A 2010-276687 discloses an electronic cassette of wireless type which is provided with a wireless communication section and a battery, so that a communication cable or a power cable is unnecessary, in order to improve handling of the electronic cassette. A rechargeable secondary battery is used as an internal battery.

FIG. 10 in JP-A 2010-276687 shows an electronic cassette charger. The charger is provided with a loading chamber into which the housing of the electronic cassette is insertably/removably loaded. An insertion opening of the loading chamber is formed on an upper surface of a main body of the charger and the cassette is inserted from above. In spite of no description in JP-A 2010-276687, an inside of the loading chamber is generally a rectangular shaped box and a bottom of the loading chamber is provided with a connecter electrically connected to the internal battery of the electronic cassette for supplying power to the built-in battery. When the electronic cassette is inserted from the insertion opening, the connecter of the electronic cassette and the connecter of the charger are connected to start charging.

However, rubbish or dust is easy to enter the loading chamber of the charger through the insertion opening and it is likely to accumulate on the bottom of the loading chamber. When the rubbish or dust adheres to the connecter, problem of contact failure occurs since the connecter is provided on the bottom surface.

The electronic cassette charger is a medical equipment used in medical facilities such as a hospital, so that there is a concern that fluid such as body fluid or blood or medicines, other than rubbish or dust, is entered from the insertion opening. Since the connecter is an electric component, avoiding enter of the fluid is highly required more than that of the dust or rubbish. Therefore solution for solving the above problems has been strongly desired. JP-A 2010-276687 does not disclose any indication or suggestion in relation to the above problem and its solution.

SUMMARY OF THE INVENTION

An object of the present invention is to provide an electronic cassette charger which allows less dirt adhesion to a connecter in a loading chamber.

In order to achieve the above object and others, the charger of the present invention is provided with a main body, a loading chamber, a bottom surface of the loading chamber and a connecter, and charges a battery in a battery container. The main body contains a charge circuit. The loading chamber is formed in the main body and insertably/removably contains the battery container. The insertion opening is formed at an entry of the loading chamber. The bottom surface of the loading chamber has first and second ends (corners), and inclines with respect to the horizontal direction so that the first end is located higher than the second end. The connecter is located on the bottom surface with an interval from the second end, and connects the battery to the charge circuit when the battery container is loaded into the loading chamber.

The connecter is preferably located between the center of the bottom surface and the first end. In the bottom surface, the second end is preferably positioned to the front surface side of the main body and the first end is preferably positioned to the back surface side of the main body. Moreover, the loading chamber is preferably inclined toward the front surface of the main body. The insertion opening is preferably inclined to the same direction as the bottom surface. In this case, the inclined angle of the insertion opening may be approximately same as that of the bottom surface, or may be larger than that of the bottom surface. Preferably, the loading chamber has inner wall surfaces to face the front surface and back surface of the main body, inclined toward the front surface of the main body, and the front and back surfaces are inclined in a direction same as the inner wall surfaces.

It is preferable that a lower surface of the main body extends in an almost horizontal direction, a space between the lower surface and the bottom surface enlarges to the first end from the second end. The insertion opening is, for example, a long and thin hole extending in a front and back direction of the main body. Further, the battery container is, for example, an almost rectangular flat plate and the loading chamber is, for example, a thin box shape. The battery container may be a battery pack that is detachably attached to the electronic cassette, or may be the electronic cassette incorporating the battery.

In the present invention, the bottom surface of the loading chamber into which the battery container is loaded is inclined with respect to the horizontal direction, and the connecter is located on the bottom surface apart from the second end, so that rubbish or dust entered into the loading chamber accumulates to the second end side, and less dirt adheres to the connecter.

BRIEF DESCRIPTION OF THE DRAWINGS

The above objects and advantages of the present invention will become easily understood by one of ordinary skill in the art when the following detailed description would be read in connection with the accompanying drawings.

DESCRIPTION OF THE PREFERRED EMBODIMENTS

First Embodiment

Figure 1:
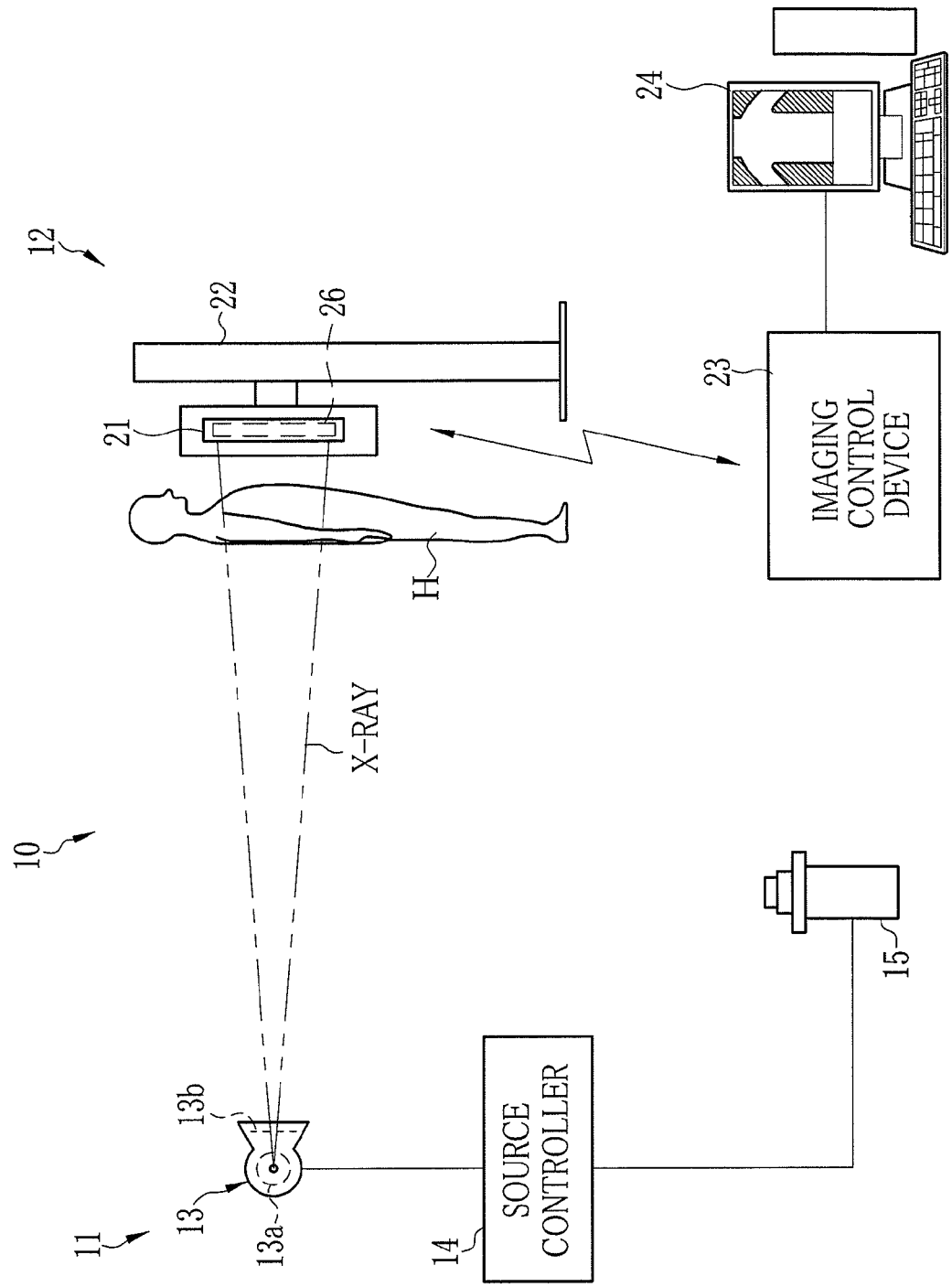
FIG. 1 is a schematic diagram illustrating an X-ray imaging system.

In FIG. 1, an X-ray imaging system 10 includes an X-ray generation device 11 and an X-ray imaging apparatus 12. The X-ray generation device 11 is constituted of an X-ray source 13, a source controller 14 for controlling the X-ray source 13, and an irradiation switch 15. The X-ray source 13 has an X-ray tube 13a for irradiating X-rays and an irradiation field limiter (collimator) 13b for limiting irradiation field of X-rays irradiated from the X-ray tube 13a.

The X-ray tube 13a has a cathode made of filament which emits thermal electrons and an anode (target) which irradiates X-rays after collision of the thermal electrons emitted from the cathode. The irradiation field limiter 13b is made of, for example, plural lead plates for shielding X-rays except for a middle portion. An irradiation opening for transmitting X-rays is formed in the middle portion of the irradiation field limiter 13b, in which the size of the irradiation opening is changed by moving the position of the lead plates to limit irradiation field.

The source controller 14 includes a high voltage generator for supplying high voltage to the X-ray source 13, tube voltage for determining energy spectrum of X-rays emitted from the X-ray source 13, tube current for determining amount of irradiation per hour, and a controller for controlling irradiation time of X-rays. The high voltage generator boosts input voltage by a transformer, generates high-pressure tube current, and supplies driving power to the X-ray source 13 through a high voltage cable. photographic conditions, for example, tube voltage, tube current and irradiation time are manually set by an operator such as a radiologist through an operation panel of the source controller 14, in addition, set through the communication cable from the X-ray imaging apparatus 12.

An irradiation switch 15 is operated by the radiologist and connected to the source controller 14 via a signal cable. The irradiation switch 15 is a two step button, in which warm-up initiation signal for initiating warm-up of the X-ray source 13 is generated at the first step, and irradiation initiation signal for initiating irradiation from the X-ray source 13 is generated at the second step. These signals are input to the source controller 14 via the signal cable.

The source controller 14 controls operation of the X-ray source 13 based on a control signal from the irradiation switch 15. When radiation initiation signal is received from the irradiation switch 15, the source controller 14 starts power supply to the X-ray source 13 and operates timer to start measurement of irradiation time of X-rays. When irradiation time set under the photographic condition passes over, the source controller 14 stops irradiation of X-rays. Irradiation time of X-rays changes according to photographic condition. In a case of photographing of still image, maximum irradiation time of X-rays is generally set between 500 millisecond to 2 second, then this maximum irradiation time is set as an uppermost limit.

The X-ray imaging apparatus 12 includes an electronic cassette 21, a photography platform 22, an imaging control device 23 and a console 24. The electronic cassette 21 is a transportable radiation image detector, including FPD 26 and a housing 27 for housing the FPD 26, and detects X-ray image of a patient H (object) after receiving X-rays that is irradiated from the X-ray source 13 and transmitted through patient H. The electronic cassette 21 has flat-plate housing. The housing is thin box shape and its flat surface size is almost same as a film cassette or an IP cassette.

The photography platform 22 has a slot into which the electronic cassette 21 is detachably attached, and holds the electronic cassette 21 in a manner that X-rays incident surface faces the X-ray source 13. Since the case 27 is almost same as the film cassette and IP cassette in size, the electronic cassette 21 can be attached to the platform for the film cassette or IP cassette. It is noted that an upright posture radiographic stand that photographs the patient H at upright position is described as an example of the photography platform 22, but a supine posture radiographic stand may also be used that photographs the parent H at supine position.

Further, in case of photographing of hands or legs of the patient H which is hard to be photographed in a manner that the electronic cassette 21 is attached to the photography platform 22, the electronic cassette 21 is used detached from the photography platform 22.

The electronic cassette 21 is wireless type and includes a wired communicator using a communication cable as a communicator for communicating with the imaging control device 23 and a wireless communicator for communicating via electric wave or ray (for example, infrared ray). Moreover, the electronic cassette 21 is driven by battery in addition to by commercial power supply using power cable. The wireless type electronic cassette 21 is easy to use since the cable is unnecessary.

The imaging control device 23 is connected to the electronic cassette 21 with wire communication or wireless communication and controls the electronic cassette 21. In particular, photographic condition is sent to the electronic cassette 21 to set processing condition of signal process of the FPD 26 (for example, gain of amplifier for amplifying voltage according to accumulated signal charge). Simultaneously, synchronized signal for synchronizing irradiation timing of the X-ray source 13 and accumulated operation of the FPD 26 is received from the X-ray generation device 11 and sent to the electronic cassette 21 to perform synchronized control of the X-ray source 13 and the FPD 26. The imaging control device 23 receives image data output from the electronic cassette 21 and send it to the console 24.

The console 24 receives input of inspection order including information of gender, age, body part, purpose of photography and so on, and displays the inspection order on a display. The inspection order is input from a exterior system which manages inspection information in relation to patients' information or radiological inspection such as HIS (hospital information system) or RIS (radiography information system). Alternatively, the inspection order is manually input by an operator. The operator confirms content of the inspection order on the display and selects the photographic condition according to the content through an operation screen of the console 24. The selected imaging condition is sent to the imaging control device 23.

The console 24 sends photographic condition to the imaging control device 23 and performs image processing to X-ray image data sent from the imaging control device 23. The processed X-ray image is displayed on the display of the console 24, and data of the X-ray image is stored in a hard disc or memory in the console 24, or a data storage device such as image accumulation server connected to the console 24 via network.

Figure 2:
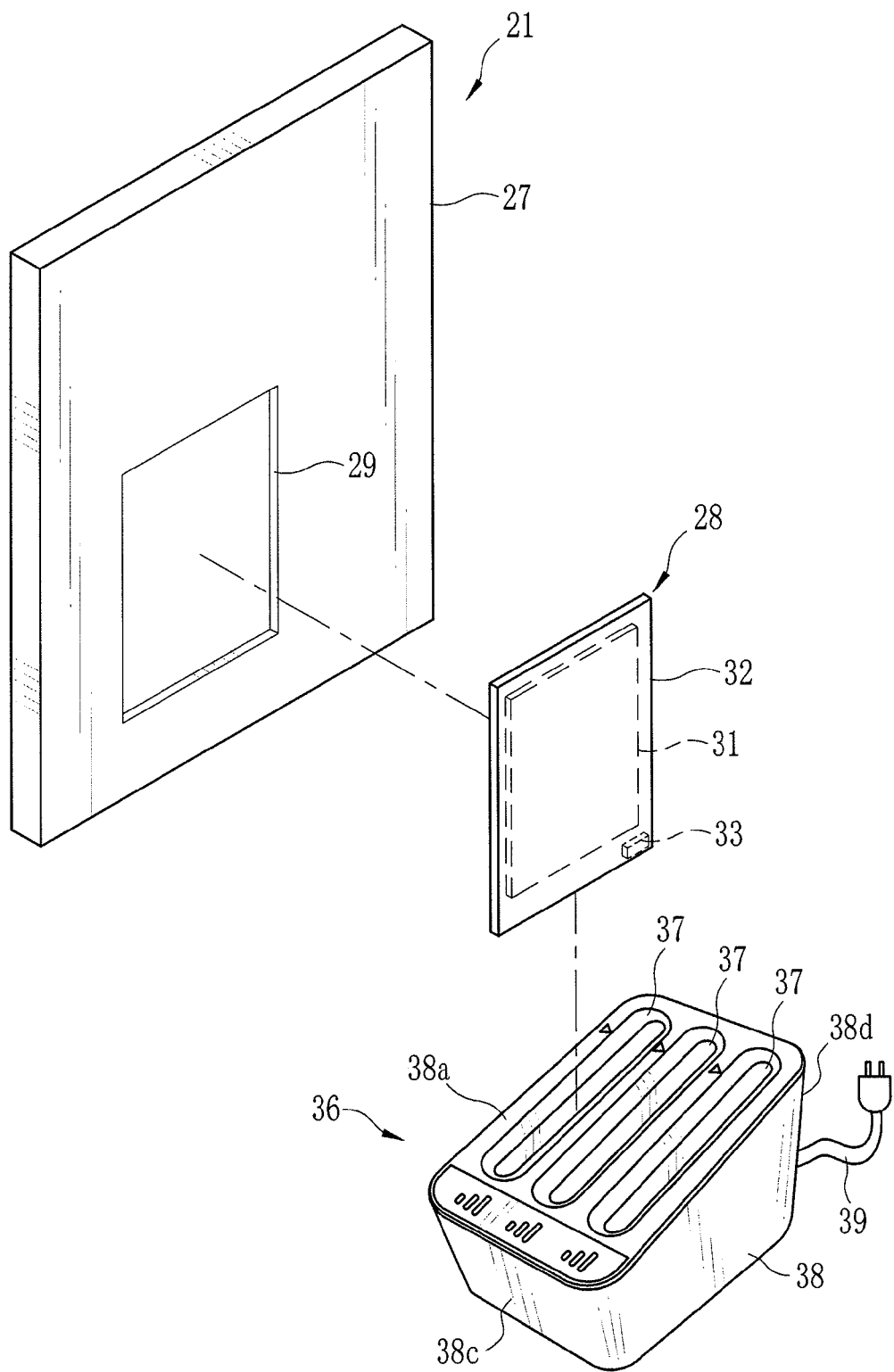
FIG. 2 is a perspective view illustrating an electronic cassette and a charger.

Shown in FIG. 2, a back surface of the housing 27 of the electronic cassette 21 is provided with an attachment part 29 to which a battery pack 28 is detachably attached. The battery pack 28 is a battery container including a battery 31 for supplying power for driving the FPD 26 and the communicator, and a case 32 for containing the battery 31. The case 32 of the battery pack 28 is a rectangular flat plate so as to be attached to the flat housing 27 of the electronic cassette 21.

The battery 31 is a rechargeable, for example, lithium secondary battery. The battery pack 28 is removed from the electronic cassette 21, loaded into a charger 36 and charged. The battery pack 28 has a connecter 33 for receiving power supplied from the charger 36. The connecter 33 is disposed at one corner of the case 32. A connection terminal (see symbol 33*a* of FIG. 4) that is a contact point for conduction of the connecter 33 is exposed from a short side of the rectangle-shaped case 32.

The charger 36 includes a box-shaped main body 38 provided with a loading chamber 37 into which the battery pack 28 is insertably/removably loaded, and a power cable 39 for connecting to commercial power. The charger 36 has three loading chambers 37, and is allowed to recharge three battery packs 28 at a same time. The loading chambers 37 are shaped so as to insert the flat board-shaped battery packs 28. The battery pack 28 is inserted in the loading chambers 37 in a manner that one short side from which the connecter 33 is exposed is downwardly oriented.

Figure 3:
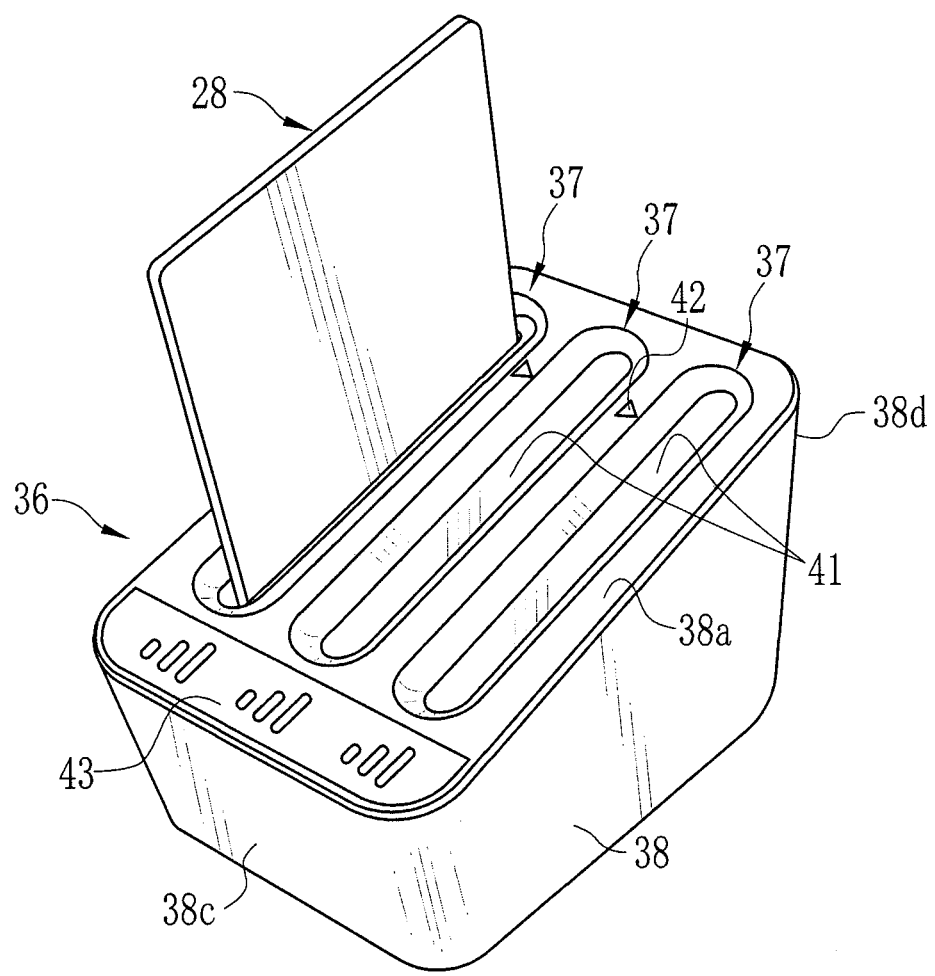
FIG. 3 is perspective view illustrating the charger in a manner that a battery pack is charged.

Shown in FIG. 3, the insertion opening 41 of the loading chamber 37 is a narrow and long opening extending in a front and back direction of the main body 38, formed on an upper surface 38*a* of the main body 38 and opens upwardly. The insertion opening 41 has a length corresponding to a short side of the battery pack 28. The three insertion openings 41 are arranged in a manner that longitudinal sides thereof are adjacent each other. The upper surface 38*a* inclines with respect to the horizontal direction so that the front surface 38*c* of the main body 38 is located at a lower end and a back surface 38*d* of the main body 38 is located an upper end. Since the insertion openings 41 are formed on the upper surface 38*a*, the insertion openings 41 incline so that one end of the insertion openings 41 in a longitudinal direction is located at upper end and the other end thereof is located at lower end, in a similar to inclination of the upper surface 38*a*, the insertion openings 41 have an angle in a same direction as the upper surface 38*a*.

The battery pack 28 is inserted from the insertion openings 41 and fixed in a manner that the lower part thereof is contained in the loading chamber 37. The charger 36 is capable of self-standing in a manner to hold the battery pack 28. Since the insertion openings 41 are upwardly oriented, an operator can insert the battery pack 28 into the charger 36 so as to drop the battery pack 28 in the insertion openings 41, so that smooth insertion can be achieved.

Further, since the insertion openings 41 inclines so as to uprise in a direction of the front surface 38*c*, the insertion openings 41 orient to the operator who faces the front surface 38*c* of the main body 38, so that the insertion openings 41 is easily viewable.

An opening rim of the insertion opening 41 opens in U-shaped manner and becomes a guide surface for directing the battery pack 28 to the back of the insertion openings 41. Marks 42 are provided beside each of the insertion openings 41 for matching direction of the battery pack 28. The marks 42 are confirmed by the operator and the orientation of the battery pack 28 can be matched in a front-back direction so as to correspond to the position of the marks 42 and the connecter 33.

The upper surface 38*a* is provided with indicators 43 for displaying a state-of-charge of the battery pack 28 at the lower end of the 41 (at the side of the front surface 38*c*). Each of the indicators 43 is a set of three lamps having different lengths which illuminates one by one in order of shortest one according to progress of charging and displays the progress in stages.

Figure 4:
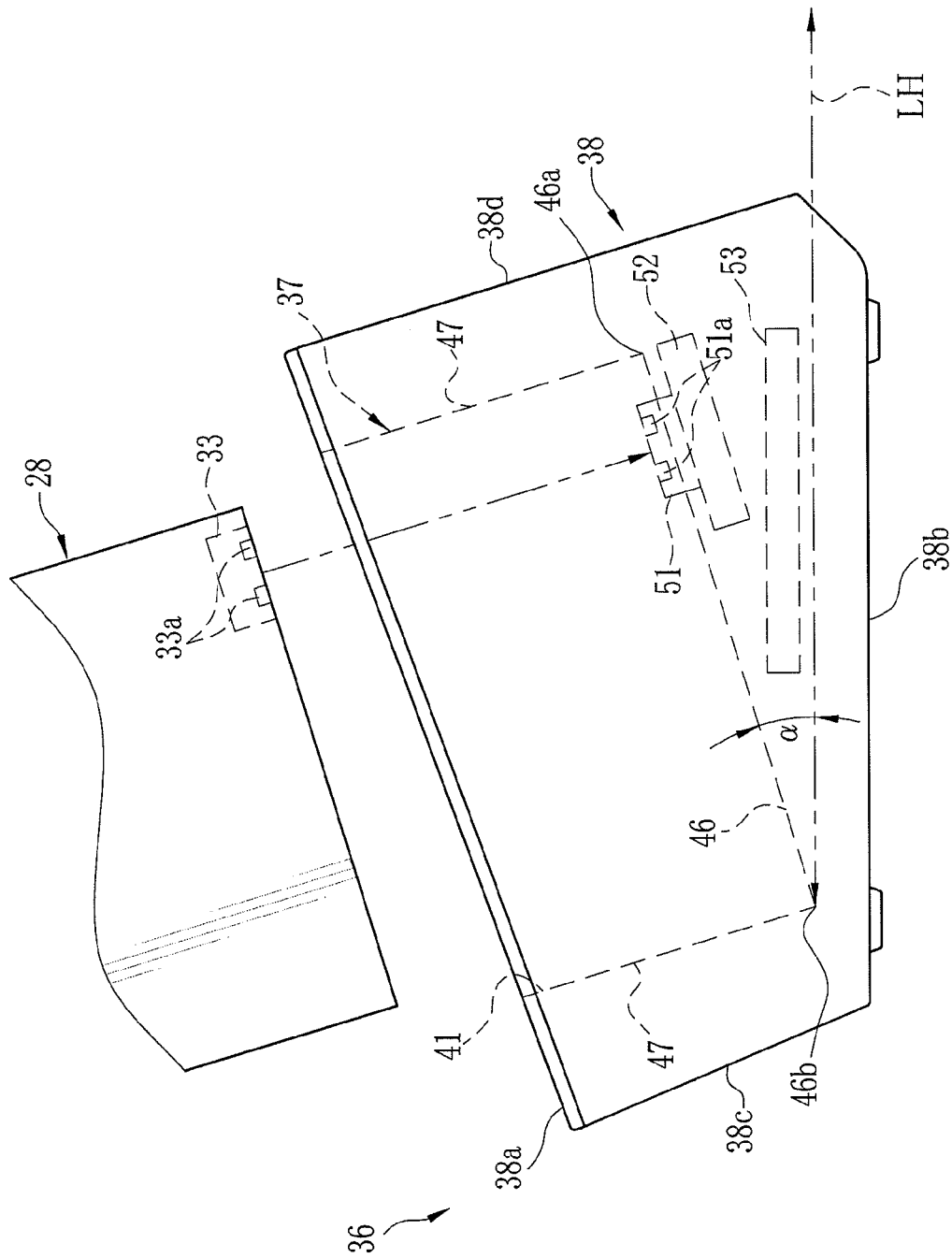
FIG. 4 is an explanatory drawing illustrating an loading chamber.

Shown in FIG. 4, a bottom surface 46 is provided in the depth of the insertion opening 41 inside the loading chamber 37. An inner wall surfaces stands toward the insertion opening 41 from the bottom surface, so that the inner wall surface and the bottom surface 46 configure an inner surface of the loading chamber 37. The inner wall surface is almost perpendicular to the bottom surface 46, and the loading chamber 37 is rectangular shape seen from lateral side shown in FIG. 4, corresponding to the shape of the battery pack 28.

The loading chamber 37 entirely inclines forwardly corresponding to the inclination of the upper surface 38*a* and the insertion opening 41, in which each of the inner wall surfaces 47 which vertically stands from the upper (upper corner) 46*a* end and lower end (lower corner) 46*b* of the bottom surface 46 also inclines forwardly toward the front surface 38*c* of the main body 38. When the loading chamber 37 inclines forwardly, insertion posture at the time of inserting the battery pack 28 into the insertion opening 41 is lying posture to orient the upper part of the battery pack 28 to face the operator, so that the upper part of the battery pack 28 is close to the operator and the operator is easy to hold the battery pack 28. Therefore, smooth insertion can be achieved compared to the case where the case 27 does not forwardly incline.

Moreover, when the loading chamber 37 inclines forwardly, the battery pack 28 loaded into the loading chamber 37 also inclines forwardly. Therefore, the battery pack 28 can be smoothly removed since the upper end of the battery pack 28 orients toward the front surface 38*c*.

Each of the inner wall surfaces 47 at the front and back faces the front surface 38*c* and the back surface 38*d*, and the front surface 38*c* and the back surface 38*d* incline in a direction same as each of the inner wall surfaces 47. The front surface 38*c* and back surface 38*d* incline in a direction same as the loading chamber 37 and show loading posture of the battery pack 28 loaded into the loading chamber 37 in a same manner to the insertion opening 41. Therefore, it is easy to guess the attachment posture of the battery pack 28 from the appearance of the main body 38. If the attachment posture can be guessed, determination of the insert position of the battery pack 28 to the insertion opening 41 is easy, so that smooth insertion of the battery pack 28 can be achieved.

It is noted that if the inner wall surface 47, front surface 38*c* and back surface 38*d* incline in a same direction, namely toward the front surface 38*c*, approximate loading posture of the battery pack 29 can be guessed despite of some slight difference of the inclined angles there between, so that the inclined angles are not necessary to be consistent with each other.

The bottom surface 46 is a surface where one side provided with the connecter 33 of the battery pack 28 contacts, and is provided with a connecter 51 connected to the connecter 33. The connecter 51 has a connection terminal 51*a* which contacts the connection terminal 33*a* of the connecter 33 to be electrically conducted, and the connection terminal 51*a* exposes from the bottom surface 46. When the battery pack 28 is loaded into the loading chamber 37, the connecter 33 and the connecter 51 engage and the connection terminal 33*a* and the connection terminal 51*a* contact to electrically connect the charger 36 and the battery pack 28. Thereby, the charging of the 31 used by the charger 36 starts.

Since the loading chamber 37 forwardly inclines toward the front surface 38*c*, the bottom surface 46 also inclines with respect to a horizontal direction so that one end is located at upper end and the other end is located at lower end in a similar manner to the upper surface 38*a* and the insertion opening 41, in which inclined angle α shows angle to phantom horizontal line LH. The lower end of the bottom surface 46 is positioned at the side of the front surface 38*c* and the upper end is positioned at the side of the back surface. The bottom surface 46, the upper surface 38*a* and the insertion opening 41 are almost horizontal, in addition, the inclined angle of the upper surface 38*a* and the insertion opening 41 are similar to the inclined angle α of the bottom surface 46.

The connecter 51 is disposed to have intervals from the lower end 46*b* of the charger 46. In particular, the connecter 51 is disposed to the upper stream side which is between the central portion of the bottom surface 46 and the upper end 46*a*, so as not to be located higher than the lower end 46*b*, on the basis of the phantom horizontal line LH. Thereby, a space for accumulating rubbish, dust or fluid which is downwardly flowed is obtained at the downstream of the connecter 51. Therefore, if the rubbish, dust or fluid is entered from the insertion opening 41 and downwardly flowed to the bottom surface 46, the rubbish, dust or fluid gathers to the lower end 46*a* of the connecter 51 and less dirt adheres to the connection terminal 51*a*.

Since a small size is ideal for a space where rubbish, dust or fluid falls at the upstream side of the connecter 51, it is preferable that the connecter 51 is disposed within the range about one to forth from the upper end 46*a* in all length between the lower end 46*b* and the upper end 46*a* of the bottom surface 46. From a point view of reducing the space, the connecter 51 is better to be positioned at near the upper end 46*a*. In case of locating the connection terminal 51*a* at the upper end 46*a*, the connecter may be partly provided on the inner wall surface that perpendicularly stands from the bottom surface 46.

The connector substrate 52 to which the connecter 51 is attached and electric parts such as a main substrate 53 connected to the power cable 39, formed with charging circuit including a rectifier and a regulator are located in space between the bottom surface 46 and the lower surface 38*b*. The connector substrate 52 and the main substrate 53 are connected via wiring such as wiring harness.

While the lower surface 38*b* extends in a horizontal direction, the bottom surface 46 inclines. Therefore the space between the bottom surface 46 and the lower surface 38*b* enlarges from the lower end 46*b* to the upper end 46*a* of the bottom surface 46. Therefore, a large space exists between the upper end of the bottom surface 46 and the lower surface 38*b*, i.e. a lower side of the 51. In case of attachment of the connecter 51, storage for disposing the connector substrate 52 is required at lower side of the connecter 51, so that existing of large space at lower side of the connecter 51 is beneficial for layout of parts.

This can prevent increase of the size of the main body 38. For example, in case where the connecter 51 is disposed at the lower end 46*b* of the bottom surface 46, securing a large space for locating the connector substrate 52 is required between the bottom surface 46 and the lower surface 38*b*. However, if the connecter 51 is disposed at the upper end 46*a* of the bottom surface 46, it is not necessary to secure the space. Therefore, the height of the main body 38 can be controlled.

Figure 5:
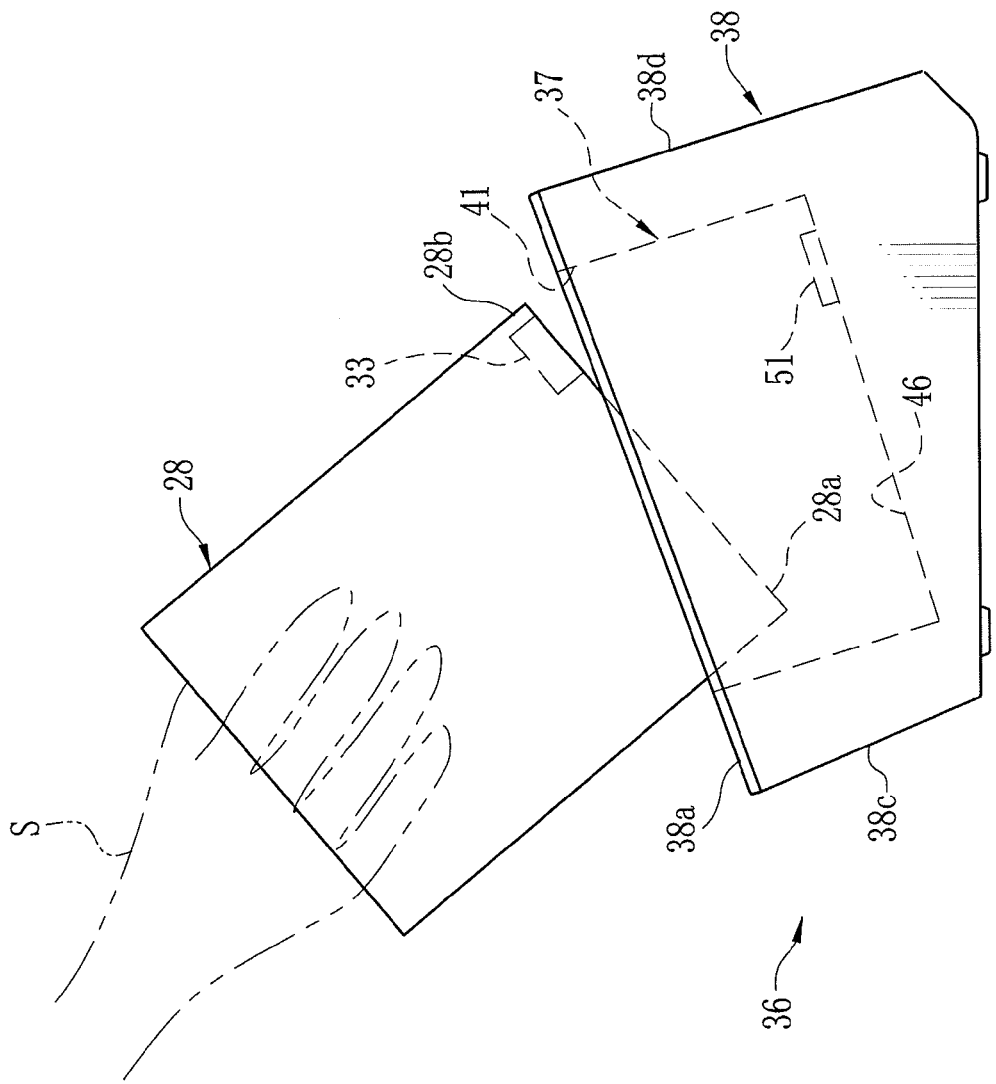
FIG. 5 is an explanatory drawing illustrating an insertion angle of the battery pack.

The operation of the above construction is described now with reference to FIG. 5. In medical facilities, the charger 36 is set in a photo studio where X-ray source and platform is set, an operation room next to the photo studio, or a device storage room. Since the insertion opening 41 of the charger 36 orients obliquely upward, rubbish, dust or fluid is easy to enter inside of the loading chamber 37 from the insertion opening 41. Moreover, rubbish, dust or fluid which adheres to the battery pack 28 occasionally enters the loading chamber 37 when the battery pack 28 is loaded into the loading chamber 37.

Since the connecter 51 is disposed apart from the lower end 46*b* in the inclined bottom surface 46, rubbish, dust or fluid flows down to the lower end 46*a* of the connecter 51 by action of gravity, and is not carried in the vicinity of the connection terminal 51*a* of the connecter 51. Consequently, less dirt adheres to the connection terminal 51*a*. Therefore, contact failure of the connecter 51 due to corrosion resulting from adhesion of dirt can be prevented.

When electric quantity of the battery 31 of the electronic cassette 21 reduces, the battery pack 28 is removed from the electronic cassette 21 and loaded into the charger 36. When the battery pack 28 is loaded in the charger 36, the operator faces the front surface 38*c* of the main body 38 and holds the battery pack 28 so that the connecter 33 downwardly orients as shown in FIG. 5. The insertion opening 41 inclines so as to stand toward the front surface 38*c* and orients to the operator who faces the battery pack 28, so that the operator is easily viewable.

The operator checks the marks 42 (see FIG. 3) near the insertion opening 41 and matches the front and back direction of the battery pack 28 so as to match the position of the marks 42 and the connecter 33. Then, the insertion position of the battery pack 28 is determined according to inclination of the loading chamber 37 to insert the battery pack 28 from the insertion opening 41.

Since the insertion opening 41 and the bottom surface 46 incline in an almost same direction and the front surface 38*c* and the back surface 38*d* of the main body 38 incline in a same direction as the inner wall surface 47 of the loading chamber 37, it is easy to imagine the loading posture of the battery pack 28 from the appearance of the main body 38. Therefore, it is easy to match the insert posture of the battery pack 28 with the loading posture, so that smooth insertion can be achieved.

When the object having plural angles such as rectangular object is inserted into the opening, it is empirically known that the operator tends to insert the nearest corner of the object at the beginning. Particularly, when the flat plate shaped object such as the battery pack 28 is inserted in the narrow and long opening, for example, the insertion opening 41, the operator tends to insert the object from the nearest corner thereof. Shown in FIG. 5, a corner 28*a* that is nearest corner seen from the operator is inserted through the insertion opening 41 at the beginning, which is selected from the corners 28*a* and 28*b* of the battery pack 28 which face the insertion opening 41. In order to insert the corner 28*a* into the insertion opening 41, insert posture of the battery pack 28 is more inclined compared to the loading posture of the battery pack 28 so that the upper part of the battery pack 28 faces the operator.

Since at the front and back direction of the battery pack 28 is set so that the corner 28*b* having the connecter 33 is located to the upper end of the insertion opening 41, the connecter 33 does not exist at the corner 28*a* that is nearest corner seen from the operator.

When the corner 28*a* of the battery pack 28 is inserted into the insertion opening 41, the corner 28*a* firstly approaches the bottom surface 46 in the loading chamber 37 and the corner 28*a* possibly hits to the bottom surface 46. Since the battery pack 28 is comparatively heavy, the corner 28a sometimes hits to the bottom surface 46 by mistake upon insertion. In particular, in case of a loading chamber 37 having the long and thin insertion opening 41, since it is difficult to estimate the depth from the insertion opening 41 to the bottom surface 46, the corner 28a tends to hit to the bottom surface 46. However, also in the above case, the connecter 33 is not provided at the corner 28a and the connecter 33 is not damaged due to hit.

Moreover, the corner 28a is placed at front side, so that the corner 28a is likely to hit to the lower end side of the bottom surface 46. However, the connecter 51 of the charger 36 is provided to the upper end 46a side which is far side from the operator, and a connecter 51 is not disposed to the lower end 46b of the bottom surface 46 to which the battery pack 28 is possibly hit. Therefore, when the corner 28a accidentally hits to the bottom surface 46, the corner 28a does not hit to the connecter 51, so that the connecter 51 is not damaged.

The insertion opening 41 is inclined in a same direction as the bottom surface 46, the depth between the upper and 46a the lower end 46b of the insertion opening 41 and that of the bottom surface 46 are respectively same (the height between the bottom surface 46 and the insertion opening 41). Such a composition helps to prevent hit of the corner 28a and the connecter 51.

In consideration of the case that the insertion opening 41 extends in a horizontal direction without inclination in spite of inclination of the bottom surface 46, the upper end of the bottom surface 46 where the connecter 51 is located is depthless as compared to the lower end side of the bottom surface 46 where the connecter 51 is not located. If the connecter 51 is depthless from the insertion opening 41, the corner 28a which firstly enters from the insertion opening 41 is at risk for accidentally hitting to the connecter 51 which is located depthless position. As in the present invention, since the depth between the insertion opening 41 and the upper end side of the bottom surface 46 where the connecter 51 is located is almost same as the depth between the insertion opening 41 and the lower end side of the bottom surface 46 when the insertion opening 41 is inclined in a same direction as the bottom surface 46, the risk for hit can be reduced. When the battery pack 28 is inserted into the loading chamber 37, the battery 31 is connected to the charge circuit via the connecter 51, and the battery 31 is charged, as is well known in the art.

Second Embodiment

Figure 6:
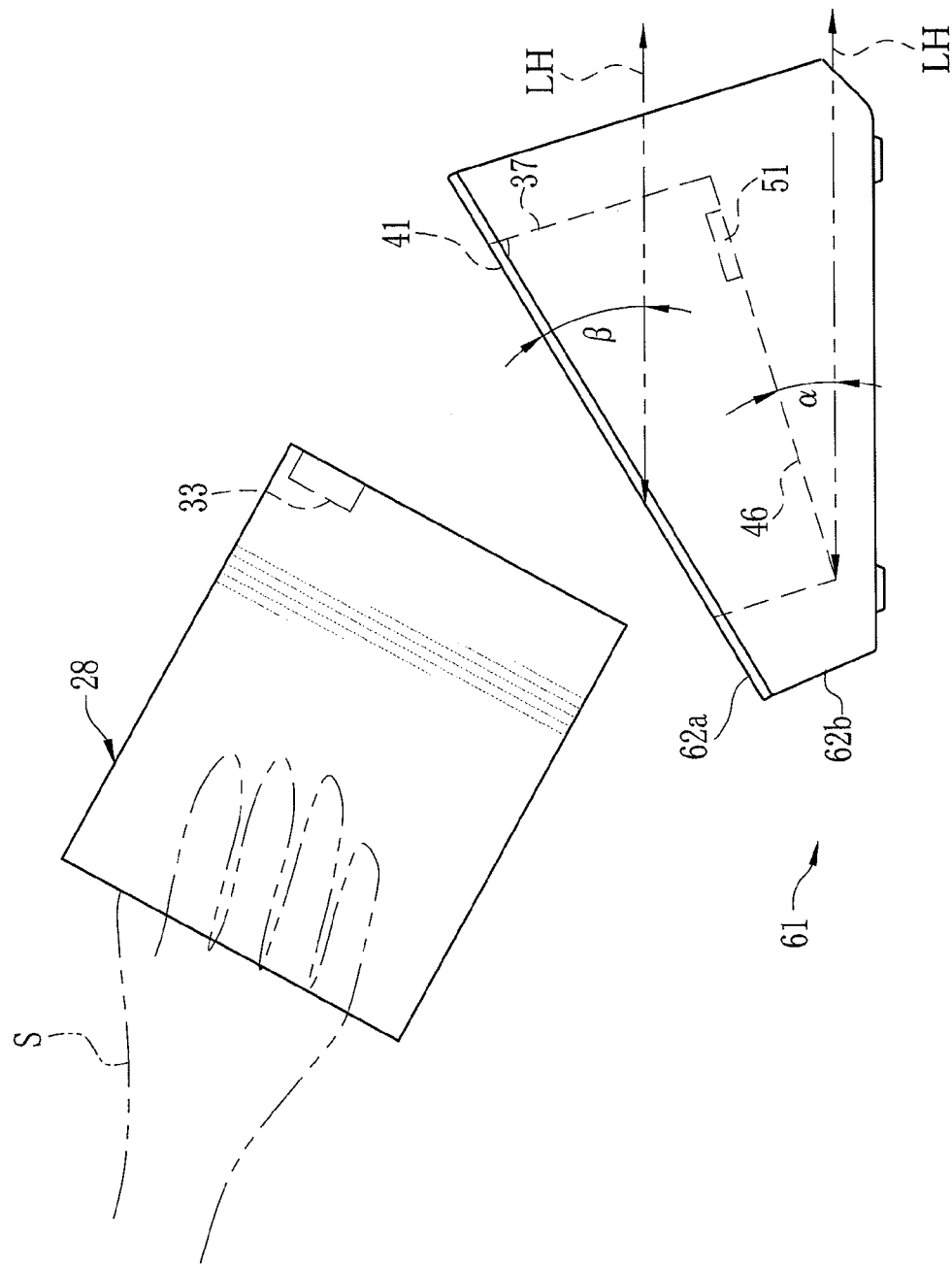
FIG. 6 is an explanatory drawing illustrating that the insertion opening is inclined larger than the bottom surface of the loading chamber.

In the above first embodiment, the insertion opening 41 is inclined in a same direction as the bottom surface 46, and the inclined angle of the insertion opening 41 is almost same as the inclined angle α of the bottom surface 46. However, as shown in a charger 61 of the second embodiment of FIG. 6, an inclined angle β (inclined angle to phantom line LH which extends in a horizontal direction) of the insertion opening 41 formed on an upper surface 62a of a main body 62 may be larger than inclined angle α of the bottom surface 46, i.e. α<β. In the result, the depth between the insertion opening 41 and the upper end side of the bottom surface 46 where the connecter 51 locates is deeper than that between the insertion opening 41 and the lower end side of the bottom surface 46, so that the risk for hitting the connecter 51 and the corner 28a can be reduced.

As described above, upon insertion of the battery pack 28 into the insertion opening 41, the operator guesses loading posture of the battery pack 28 from appearance of the main body 62 to determine insert posture of the battery pack 28. Therefore, when inclined angle of the insertion opening 41 is large in a similar manner to the charger 61, insert posture of the battery pack 28 becomes lying posture toward the operator as compared to the first embodiment shown in FIG. 4.

When the inclined angle of the battery pack 28 is larger, the distance between the connecter 33 provided to the battery pack 28 and the connecter 51 is larger. Even when the battery pack 28 is accidentally inserted into the insertion opening 41 at high speed, the risk of hitting the connecter 33 and the connecter 51 can be reduced due to the large distance. Therefore, in a similar manner to the charger 61, the inclination of the insertion opening 41 is made larger than that of the bottom surface 46, and damage caused by hitting the connecter 33 and the connecter 51 can be prevented.

It is noted that as of the charger 61 of the second embodiment, difference between the first and second embodiments is only the inclined angle of the upper surface 62a, the parts having the same structure and function as the above first embodiment have the same reference numerals, and their description will not be repeated.

Third Embodiment

Figure 7:
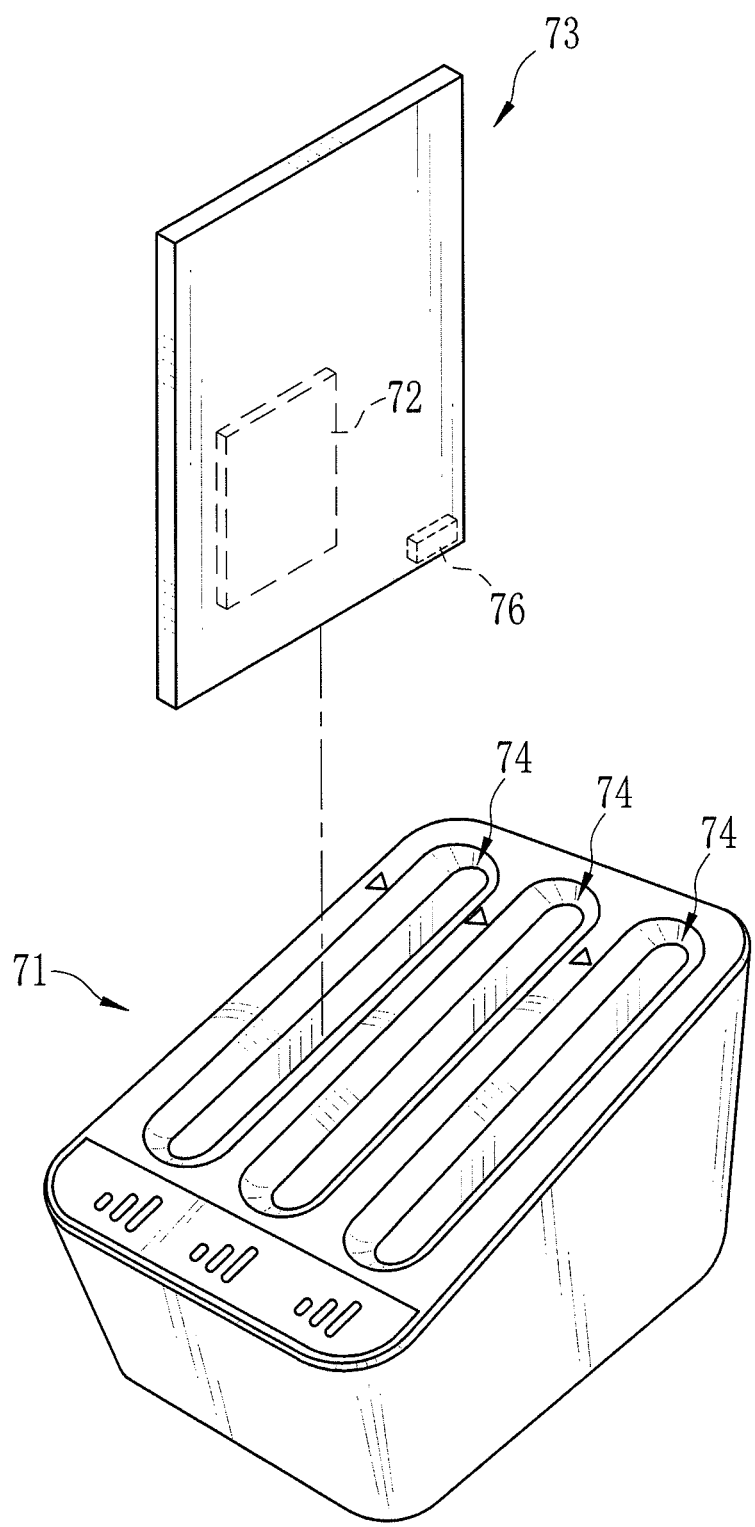
FIG. 7 is a perspective view illustrating the charger into which the electronic cassette with internal battery can be loaded.

In a third embodiment shown in FIG. 7, an electronic cassette 73 incorporating a battery 72 is entirely loaded in a loading chamber 74. In the electronic cassette 73, a connecter 76 is provided near one corner of the casing. When the electronic cassette 73 is loaded in the loading chamber 74, the connecter 76 and a connecter at the charger side in the loading chamber 74 is electrically connected. The charger 71 is different from the charger 36 and the charger 61 in size only, and the parts having the same structure and function as the above first embodiment have the same reference numerals, and their description will not be repeated.

In the above embodiments, the example that the insertion opening 41 and the bottom surface 46 are inclined in a same direction, but the insertion opening 41 may extend in a horizontal direction without inclination or may be inclined in a direction opposite to the bottom surface 46. The result for preventing contact failure of the insertion opening 41 is obtained by disposing the connecter 51 at the upper end side of the bottom surface 46 which is inclined, in which the result is obtained regardless of whether the inclination of the insertion opening 41 presents or not, or the inclined direction of the insertion opening 41.

Moreover, in the above embodiments, the example that the insertion opening 41 is provided on the upper surface 38a of the main body 38 is described, but the insertion opening 41 may be provided on the front surface 38c of the main body 38. This is because result for preventing contact failure of the connecter 51 can be obtained if the bottom surface 46 is inclined even if the insertion opening 41 having opening in a horizontal direction is formed on the front surface 38c. It is noted that when the insertion opening 41 is provided on the front surface 38c, the front surface 38c may be inclined to the back surface 38d to orient the insertion opening 41 in an upper direction. This is because the easy insertion of the battery pack 28 can be obtained as in the above embodiments.

Moreover, in case of the charger 61 of the second embodiment, the inclined angle β of the insertion opening 41 is larger than the inclined angle α (α<β), but it may be possible that the inclined angle β of the insertion opening 41 is smaller than the inclined angle α (α>β) since visibility of the insertion opening 41 can be improved if the inclined direction of the insertion opening 41 is same as that of the bottom surface 46.

Furthermore, in the above embodiments, the flat plate-shaped battery container whose planar shape is almost rectangular is used, but the shape of the battery container is not limited to the above embodiments, for example, a thick block-shaped battery container may be used. A side of the battery container which configures the battery container, provided with the connecter 33 may be curved in an arc manner. The shape of the loading chamber 37 including the insertion opening 41, the bottom surface 46, and the inner wall surface 47 is determined according to the shape of the battery container. Still further more, the example that the insertion opening 41 is formed on the upper surface of the main body is described, but the insertion opening 41 may be partly formed on the front surface or back surface of the main body. It may be also possible that the upper surface, the front surface and the back surface are configured with continuous curved surface.

In the above embodiments, the example that the connecter 51 is disposed at the upstream side which is between the center and the upper end of the bottom surface 46 is described, but the connecter 51 may be disposed at the downstream side which is between the center and lower end of the bottom surface 46. If the connecter 51 is apart from the lower end 46*b* of the inclined bottom surface 46, a space for accumulating rubbish, dust or fluid which is flown down from the connecter 51 side is formed, so that less dirt adheres to the connection terminal 51*a*.

While the battery container such as the battery pack 28 or the electronic cassette 73 is not loaded into the loading chamber 37, a shutter may be provided for covering the insertion opening 41 and preventing enter of dust, rubbish, fluid in the insertion opening 41. The shutter is biased by an elastic material such as a spring at the position to cover the insertion opening 41, and opened by press of the battery container inserted into the insertion opening 41. It is noted that the shutter is difficult to have tightness (airtight or watertight) for preventing enter of dust, rubbish or fluid, so that enter of the dust, rubbish or fluid can not be prevented completely. Therefore, also in the case of providing the shutter, it is highly necessary that the bottom surface 46 is inclined and connecter is disposed at the upper end side as in the present invention in order to prevent adhesion of dirt to the connecter 51.

The present invention can be applied to a battery charger for an electronic cassette using other radial rays such as gamma rays, not limited to X-rays.

Various changes and modifications are possible in the present invention and may be understood to be within the present invention.

What is claimed is:

1. An electronic cassette charger for charging a battery in a battery container comprising:
    a main body containing a charge circuit;
    a loading chamber formed in said main body so as to insertably/removably contain said battery container;
    an insertion opening formed at an entrance of said loading chamber, for inserting said battery container;
    a bottom surface of said loading chamber, which is inclined in a longitudinal direction thereof with respect to a horizontal direction so that a first end is located higher than a second end; and
    a connector disposed on said bottom surface with an interval from said second end, for connecting said battery to the charge circuit when said battery container is loaded into said loading chamber,
    wherein said connector is disposed between the center of said bottom surface and said first end.

2. An electronic cassette charger according to claim 1, wherein said second end of said bottom surface is positioned at front surface side of said main body and said first end of said bottom surface is positioned at back surface side of said main body.

3. An electronic cassette charger according to claim 2, wherein said loading chamber is inclined toward a front surface of said main body.

4. An electronic cassette charger according to claim 3, wherein said insertion opening is inclined in a same direction as said bottom surface.

5. An electronic cassette charger according to claim 4, wherein inclined angle of said insertion opening is almost same as that of said bottom surface.

6. An electronic cassette charger according to claim 4, wherein the inclined angle of said insertion opening is larger than that of said bottom surface.

7. An electronic cassette charger according to claim 3, wherein said loading chamber has inner wall surfaces disposed to face the front surface and back surface of said main body, inclined toward the front surface of said main body, and said front surface and back surface incline in a same direction as said inner wall surfaces.

8. An electronic cassette charger according to claim 1, wherein a lower surface of said main body extends in an almost horizontal direction and a space between said lower surface and said bottom surface enlarges toward said first end from said second end.

9. An electronic cassette charger according to claim 1, wherein said insertion opening is a long and thin opening extending in a front-back direction of said main body.

10. An electronic cassette charger according to claim 9, wherein said battery container is a flat plate whose plane shape is almost rectangle, and said loading chamber is a slot.

11. An electronic cassette charger according to claim 1, wherein said battery container is a battery pack detachably attached to said electronic cassette.

12. An electronic cassette charger according to claim 1, wherein said battery container is said electronic cassette incorporating said battery.

* * * * *